US 6,588,903 B2

(12) United States Patent
Rathjen (10) Patent No.: US 6,588,903 B2
(45) Date of Patent: Jul. 8, 2003

(54) METHOD AND DEVICE CONFIGURATION FOR DETERMINING THE CORNEAL THICKNESS OF AN EYE

(75) Inventor: Christian Rathjen, Bremen (DE)

(73) Assignee: SIS AG Surgical Instruments Systems, Brugg B. (CH)

( * ) Notice: Subject to any disclaimer, the term of this patent is extended or adjusted under 35 U.S.C. 154(b) by 0 days.

(21) Appl. No.: 09/895,206

(22) Filed: Jul. 2, 2001

(65) Prior Publication Data

US 2002/0171804 A1 Nov. 21, 2002

(30) Foreign Application Priority Data

Apr. 9, 2001 (WO) .............................. PCT/CH01/00226

(51) Int. Cl.[7] .................................................. A61B 3/10
(52) U.S. Cl. ...................................................... 351/221
(58) Field of Search ................................. 351/200, 205, 351/211, 212, 221, 209; 600/558

(56) References Cited

U.S. PATENT DOCUMENTS

| | | | | |
|---|---|---|---|---|
| 5,359,373 A | * | 10/1994 | Koester et al. | 351/219 |
| 5,512,965 A | * | 4/1996 | Snook | 351/205 |
| 5,592,246 A | * | 1/1997 | Kuhn et al. | 351/212 |
| 5,812,240 A | * | 9/1998 | Teraoka et al. | 351/206 |
| 6,142,630 A | * | 11/2000 | Koester | 351/219 |
| 6,193,371 B1 | * | 2/2001 | Snook | 351/212 |

FOREIGN PATENT DOCUMENTS

DE        296 12 466 U1    11/1996

OTHER PUBLICATIONS

"Measurement Of Corneal Thickness By Low–Coherence Interferometry" by Christoph K. Hitzenberger; Applied Optics; Nov. 1, 1992, pp. 6637–6642.

* cited by examiner

Primary Examiner—Marvin M. Lateef
Assistant Examiner—John R. Sanders
(74) Attorney, Agent, or Firm—Oliff & Berridge, PLC (57) ABSTRACT

Proposed is a method and a device configuration for determining the corneal thickness of an eye, in particular of a human eye, by means of light rays. First light rays are projected onto and into the cornea, and second light rays, reflected by the cornea, are registered for determining the corneal thickness. A contact element, which is preferably plane-parallel, is placed on the contact area of the cornea, and the first light rays are projected through the contact element onto and into the cornea. The contact element is fixed on the cornea, for example. The first light rays are projected at least in points in a two-dimensional measuring area of the flattened area onto and into the cornea, and the corneal thickness is determined at one or more places of the measuring area.

30 Claims, 6 Drawing Sheets

METHOD AND DEVICE CONFIGURATION FOR DETERMINING THE CORNEAL THICKNESS OF AN EYE

BACKGROUND OF THE INVENTION

1. Field of the Invention

This invention relates to a method and a device configuration for determining the corneal thickness of an eye. In particular, this invention relates to a method and a device configuration for determining the corneal thickness of a human eye by means of light rays, first light rays being projected onto and into the cornea, and second light rays, reflected by the cornea, being registered for determining the corneal thickness.

2. Description of the Related Art

Besides the use of ultrasound for determining a human eye's corneal thickness averaged over a large range, pachymetry attachments for slit lamps are being used today to determine the corneal thickness by means of light rays. By means of a pivotable, plane-parallel plate in the path of the examination beam of a slit lamp microscope, such an attachment generates two offset half images of the light section with the cornea. By pivoting the plane-parallel plate, the offset light sections can be made congruent, and a measured value corresponding to the pivoting can be read for the cornea. Such a measurement takes place only at one point of the cornea, requires manual skill, and is difficult to reproduce since the position of the measurement point is not defined. The drawback of these methods for determining the corneal thickness is, in particular, that they are not suitable for determining corneal thickness with a high area resolution, i.e. they do not make possible determination of the corneal thickness area-wise, or in a way that completely covers the area. Consequently local deviations of the corneal thickness cannot be registered by means of these methods, which is extremely risky, and therefore disadvantageous, in particular for surgical procedures (e.g. refractive surgery).

Described in U.S. Pat. No. 5,512,965 is a device and a method based on a modified slit lamp, and by means of which a three-dimensional print-out of the cornea surface and of the respective local corneal thickness can be generated. The device according to U.S. Pat. No. 5,512,965 comprises a modified slit lamp, the projection slit of which is curved for improvement of the depth of focus, a television camera with associated lens systems, electronic circuitry for selecting and quantifying television pictures taken, as well as a control mechanism for moving the light section generated by the slit lamp. According to U.S. Pat. No. 5,512,965, a multiplicity of digitally coded pictures of the recorded light section are evaluated by means of software, measurements of individual light sections being put together via reference marks of the eye (limbus and Purkinje images of the exit pupil and highlights of the slit projector) for overall measurement. According to the method described in U.S. Pat. No. 5,512,965, the patient with the eye to be measured must focus his gaze on a target object so that eye movements that are too great can be avoided during the measurement. According to U.S. Pat. No. 5,512,965, the focus of the television camera during the measurement is updated to the cornea with an additional expense. Since the refraction of the beams, incident in the cornea, of the light section is known to depend upon the local surface inclination of the cornea, the inclination of the cornea must be measured with an additional measuring effort in order to determine the corneal thickness, in the method according to U.S. Pat. No. 5,512,965. The method according to U.S. Pat. No. 5,512,965 requires moreover a complex calibration with each measurement since the angle of illumination, the viewing angle as well as the object spacing continually change. The method according to U.S. Pat. No. 5,512,965 requires above and beyond this a complex alignment of the patient with additional marks. Owing to the high expense in technical devices, the method according to U.S. Pat. No. 5,512,965 is implemented only in the form of a standing apparatus, which has the drawback that the method is not usable for patients lying down, for example in the operating room.

The significance in ophthalmology of an area-wise corneal measurement with high resolution is clear, especially for surgical procedures on the cornea. In particular where the cornea is cut at a predefined depth or where the cornea is penetrated to a predefined depth, precise knowledge of the local corneal thickness is important. Examples of such surgical procedures are radial keratotomy, LASIK (laser in situ keratomileusis) and ALK (automated lamellar keratoplasty). Whereas in the radial keratotomy, thin superficial slits are cut into the cornea, in LASIK and ALK thin layers of the cornea are cut in flattened state of the cornea. From a medical point of view, therefore, it is extremely important to know the relevant corneal thickness prior to the operative procedure. Only with knowledge of the corneal thickness can it be ensured that an incision is not too deep and that no complications arise.

BRIEF SUMMARY OF THE INVENTION

It is an object of this invention to propose a method and a device configuration for determining the corneal thickness of an eye which at least do not have certain of the above-described drawbacks of the state of the art, and which make possible, in particular, a determination of the relevant corneal thickness of a human eye area-wise with a high area resolution. It is a further object of the present invention to reduce the expense in technical devices for determination of the corneal thickness of an eye, in order to make possible, in particular, the achievement of hand-held devices for area-wise corneal thickness measurement with a high area resolution.

These objects are achieved, according to the present invention, through the elements of the independent claims. Further preferred embodiments follow moreover from the dependent claims and from the specification.

In particular, these objects are achieved by means of the invention in that a contact element is placed on at least one contact area of the cornea, and light waves are projected through the contact element and into the cornea by a light source. Light waves, which are reflected by the cornea and the contact element, can then be registered by registering means, and a simple measurement of the thickness of the cornea is made accessible on the basis of the defined measurement conditions created by the contact element. Determination of the surface inclination of the cornea, or the curved design of projection slits to meet the Scheimpflug condition, or autofocus system for the recording means, for example, become unnecessary. Moreover the contact element makes it possible to prevent more easily undesired eye movements and deformations of the eye, for example through eye focusing, during the measurement.

In a preferred embodiment variant, the light waves, which are emitted by the light source at least in points in a two-dimensional measuring area of the contact area of the cornea on which the contact element is placed, are projected onto and into the cornea, and the corneal thickness is determined at one or more places in the measuring area. The corneal thickness can thereby be determined with a high area resolution, for example with complete coverage within the measuring area.

In a preferred embodiment variant, a contact element is used which has a predefined thickness, and the thickness of the contact element is co-used for determination of the corneal thickness. With known local thickness of the contact element using optical methods, which are based on specular reflection at the boundary surfaces of the contact element and of the cornea, and in which the thickness of the contact element can be co-established on the basis of light waves reflected by the contact element, no knowledge is required of the incidence angle of light rays at the boundary surfaces, and only the refraction indexes of the contact element and of the cornea must be known. This embodiment variant thus has the advantage that the time, effort and expense for determining the local surface inclination of the cornea in the known methods is eliminated. If, moreover, the contact element has the same refraction index as the cornea, only the ratio of the lengths of the paths has to be measured which the light waves projected into the contact element and into the cornea have taken in the contact element, or respectively in the cornea, and also methods based on light scattering or fluorescence in the cornea and in the contact element or on diffuse reflection at their boundary surfaces do not require then any knowledge of the location surface inclination. Furthermore the imaging scales, i.e. the relationship of object size to picture size, do not need to be known in order to determine the corneal thickness. Thus, for example, corneal thickness measurements can be carried out in a conventional slit lamp image with the aid of a contact lens of known thickness and with the same refraction index as the cornea.

In an embodiment variant, the cornea is brought into a defined state by means of the contact surface of the contact element, i.e. the shape and/or position of the cornea is determined by means of the contact surface of the contact element. On the basis of the defined state, which is known a priori or is determinable, depending upon the embodiment, the local surface inclination of the cornea and of the local imaging scale can be determined without high expense in technical devices. With optical methods based on specular reflection at boundary layers, the lengths of the courses of the light waves, which are dependent upon the surface inclination, in the cornea can thus be determined, and from this, the corneal thickness (perpendicular to the surface of the cornea) can be determined with knowledge of the refraction index of the cornea and of the contact element. With methods with light scattering or fluorescence in the cornea or diffuse reflection at the boundary surfaces, required in addition to the angle of incidence for the incoming light rays, are the exit angle (refraction angle) of the light rays out of the contact element as well as knowledge of the local contact element thickness and of the refraction index of the contact element and of the cornea. Moreover, in the case of non-telecentric imaging by the registering means, the contact element thickness and the imaging scale must be known. If the contact element is suitably designed, a multiplicity of these parameters can be determined simply and efficiently.

In a preferred embodiment variant, a plane-parallel contact element is used, the thickness of which is co-determined during the measurement. The use of a plane-parallel contact element has proven to be especially advantageous also for methods with light scattering or fluorescence or diffuse reflection since the above-mentioned required measurement values, respectively measurement parameters, can be obtained with a significantly lower expense in technical devices than in known methods. The use of a plane-parallel contact element for placement on the cornea makes possible embodiment variants in which the angle of illumination (angle of incidence) and the viewing angle and/or the object spacing can be kept constant (with shift, parallel to the contact element, of the measuring apparatus containing the light source and the registering means), so that a costly calibration of the measuring device configuration is eliminated. Moreover the patient does not need to be aligned in a complex way to the measuring apparatus.

In an embodiment variant, the contact element is fixed to the cornea or to the eye, for example by means of partial vacuum (suction ring). This has the advantage that a firmly defined state of the cornea is achieved and that the measuring process can be carried out more slowly since no relative movements between the eye and the contact element occur during the measurement. In addition, the fixing of the contact element to the cornea or to the eye prevents eye pressure fluctuations, for example caused by the pulse, and focusing of the eye from changing the shape and the position of the cornea.

In an embodiment variant, a semi-transparent contact element is used. A semi-transparent contact element causes incident light to be scattered so that optical methods based on light scattering or fluorescence or diffuse reflection can be applied.

In an embodiment variant, a contact element is used the refraction index of which corresponds to the refraction index of the cornea. This embodiment variant has the advantage that the corneal thickness can be determined independently of the incidence angle, or respectively the reflecting angle, of the light rays as well as independently of the refraction index for the contact elements and the cornea.

In an embodiment variant, the light source and/or the registering means are disposed according to the Scheimpflug condition in order to prevent defocusing. Through the Scheimpflug configuration sharper images can be generated, with object plane and picture plane inclined toward one another, than is possible with other configurations, for example a perpendicular disposition of the picture plane to the optical axis of the imaging system.

In an embodiment variant, the light waves projected by the light source are beamed on the cornea with a constant angle of incidence. Determination of the corneal thickness can thus be simplified since the angle of incidence has to be determined only once.

In an embodiment variant, the reflected light waves are registered at a constant viewing angle. Determination of the corneal thickness can thus be simplified since the viewing angle has to be determined only once.

In an embodiment variant, the light source is moved at a constant distance from the contact area of the contact element. The advantage of this embodiment variant is that a higher resolution, or respectively greater precision of measurement can be achieved since there are no vertical relative movements between the cornea and the light source, and light waves can be very finely focused.

In an embodiment variant, the registering means are moved at a constant distance from the contact area of the contact element. The advantage of this embodiment variant is that a higher resolution, or respectively greater precision of measurement can be achieved since there are no vertical relative movements between the cornea and the registering means, and the depth of focus area of the registering means can be designed small and thus the optical resolution high.

In an embodiment variant, the optical measuring apparatus, which comprises the light source and the registering means, is connected to the contact element, the light source and/or the registering means being movable relative to the contact element. If this connection is fixed only during the position determination of the contact element and the subsequent measurement, detachable contact elements can be used, which have different predefined thicknesses, for example, and/or are disposable.

BRIEF DESCRIPTION OF THE DRAWINGS

One embodiment of the present invention will be described in the following, with reference to an example. The example of the embodiment is illustrated by the following attached figures.

DETAILED DESCRIPTION OF THE PREFERRED EMBODIMENTS

Figure 1:
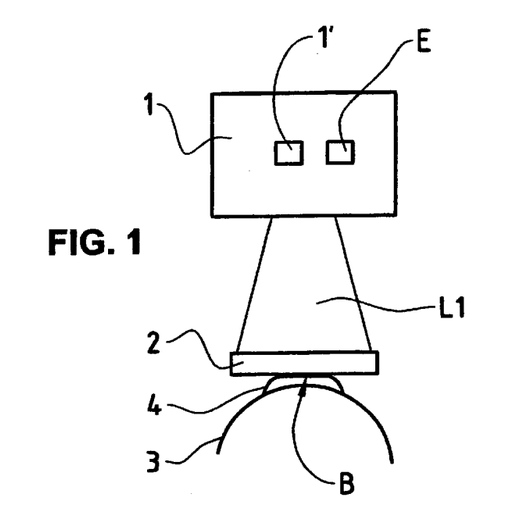
FIG. 1 shows a block diagram illustrating schematically the device configuration for determining the corneal thickness of an eye, which device configuration comprises an optical measuring apparatus, with a light source and with registering means, plus a contact element.

In FIG. 1, the reference numeral 1 relates to an optical measuring apparatus 1 with a light source 1', which projects light waves L1 onto and into the cornea 4 of the eye 3. The light source 1' is shown only schematically, and also comprises, in addition to means for generating the light waves L1, the associated imaging means, for example one or more lenses. The eye 3 is in particular a human eye. As shown in FIG. 1, a contact element 2 is placed on the cornea 4 on a contact area B of the cornea 4. The contact element 2 is preferably a plane-parallel plate of optically transparent material, for example glass or plastic, which puts the cornea 4 into a flattened state in the contact area B. Contact elements 2 curved on one side or on both sides are also possible, for example in the shape of a concave lens. A lens-shaped contact element 2 can be designed, for example, in such a way that it diverts the light waves L1 so that they strike perpendicular to the cornea 4. The contact element 2 could also be designed in such a way that it contacts the cornea 4 in a plurality of contact areas B. The light waves 1 are projected by the light source 1' through the contact element 2 and onto and into the cornea 4. The optical measuring apparatus 1 further comprises registering means E, indicated schematically, for registering light rays which are reflected by the cornea 4 and by the contact element 2. The registering means E depend upon the optical methods applied. The registering means E comprise, for example, a CCD camera, and are connected, for instance, to corresponding processing means for control and evaluation purposes.

Figure 6:
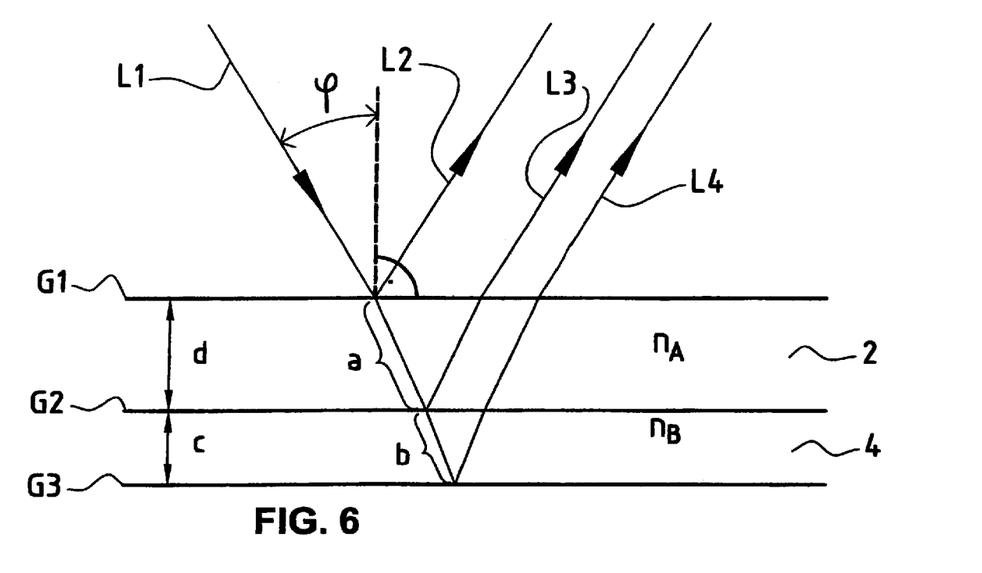
FIG. 6 shows a model of layers illustrating schematically the use of the contact element as calibrating element in determining the corneal thickness based on specular reflection at the boundary layers.

Illustrated schematically in FIG. 6 is the use of the contact element 2 as calibrating element in determining the thickness c of the cornea 4 based on specular reflection at the boundary surfaces G1, G2 and G3. The contact element 2 has a predefined thickness d (either locally, i.e. the thickness d of the contact element 2 is at least known at the points of measurement, but is not overall the same, or globally, i.e. the contact element has a constant thickness d) and a refraction index $n_A$. The refraction index of the cornea 4 is $n_B$. A light ray L1, projected by the light source 1', which stands for all the (first) light waves beamed by the light source 1', by way of example, strikes the contact element 2 with an angle of incidence Φ, and is reflected there at the boundary surface G1 partially as the light ray L2 (third light waves). The part of the light ray L1, incident in the contact element 2 and the cornea 4, takes there the additional lengths of path a, respectively b, and is partially reflected by the cornea 4 at the boundary surfaces G2 and G3. Designated by L3 or respectively L4 are the light rays reflected by the cornea 4 and emerging from the contact element 2 (second light waves). The tear film between the contact element 2 and the cornea 4 is not shown in FIG. 6 (if the thickness of the tear film were considered, there would be a reflection both at the boundary layer between the contact element and the tear fluid and at the boundary layer between the tear fluid and the cornea). It is to be noted that the light rays L1 of the light source 1' are generally not parallel to one another. The lengths of path a and b can be measured, for instance, through autofocus methods (used, for example, in CD players), through interferometric methods with minimal coherence length (optical coherence tomography—OCT; white light interferometry, e.g. by means of a Fabry-Pérot fiber optic sensors marketed by the company Fiso Technologies Inc.), through interferometric multiple wave length methods, through confocal methods with wave length-dependent focus (e.g. based on white light source and spectrometer), or methods with simple focus (measurement of the amplitude maximum, for instance by means of confocal microscope), through transit time methods (e.g. with femto pulses), or through reflection methods (e.g. according to the principle of the laser reflex sensor of the company Schäfter+Kirchhoff GmbH, Celsiusweg 15, D-22761, Hamburg, Germany) using corresponding registering means E and processing means. The thickness c of the cornea 4 results from the lengths of path a and b, from the thickness d of the contact element, as well as from the refraction indexes $n_A$ and $n_B$ of the contact element 2, respectively of the cornea 4:

$$c = b\sqrt{1 - \frac{n_A^2}{n_B^2} + \frac{n_A^2 d^2}{n_B^2 a^2}}$$

The above relationship is independent of the incidence angle $\Phi$, or respectively of the reflecting angle of equal dimension. With large or changing incidence angle $\Phi$, or respectively reflecting angle, it must be seen to it, however, that the registering means E used for the selected method is able to register all reflected rays L2, L3, L4. Depending upon the methods used, deviations occur in the measurement of a and b. In particular, deviations can occur with non-perpendicular incidence of the light waves L1. With knowledge of the incidence angle $\Phi$, these deviations can be corrected. The angle $\Phi$ can be determined, for example, with interferometric methods or transit time methods by means of the known contact element thickness d. If one derives the equations for the transit time differences of the light rays L2 and L3 shown in FIG. 6, a ratio results for determining the incidence angle $\Phi$ with the aid of the refraction law with known refraction index $n_A$ and known thickness d of the contact element 2. By using a contact element with known thickness d as reference, the advantage results therefore that the thickness c of the cornea 4 can be measured independently of the surface inclination.

With the prerequisite that the tear film (not shown) between the contact element 2 and the cornea 4 results in a sufficient reflection, or a reflection-enhancing substance is added to the tear film, or the contact element 2 is coated accordingly, the method can be further simplified in that a contact element 2 with a refraction index $n_A$ is selected corresponding to the refraction index $n_B$ of the cornea 4. Then the thickness c of the cornea 4 results from the path lengths a and b as well as from the thickness d of the contact element 2:

$$c = b\frac{d}{a}$$

It is clear that it is not the actual lengths a and b which are decisive for the measurement, but rather their ratio. Multiplicative deviations in the measurement of a and b, as can arise, for instance, through change of the incidence angle $\Phi$, thus no longer play a role.

If the refraction angle, the refraction index $n_B$ of the cornea 4 and the refraction index $n_A$ of the contact element 2 are known, the thickness c of the cornea 4 can then also be determined from the measurement value corresponding to the path length b alone. In the case of a plane-parallel contact element 2, the reflection angle can be kept constant, for example, through a parallel (translatory) displacement of the measuring head 8 used for the optical measuring method (see FIG. 4), or respectively of the light source 1'. If, furthermore, the measuring method is also dependent moreover upon the working spacing, such as, for instance, confocal methods, then the shift must be carried out in addition equidistantly. If, furthermore, the position of the contact element 2 can be determined, and if the contact surface area G2 is known sufficiently precisely, then this can be used as a reference with respect to which the surface area G3 of the cornea 4 can be measured. This is especially advantageous when the relationship of position between the measuring head 8, used for the optical measuring method (see FIG. 4), and the contact element 2 does not change. For example, an autofocus method would thus have to determine the position of the contact element 2 once only before measurement of the cornea 4, and could then measure exclusively the surface area G3.

Figure 7:
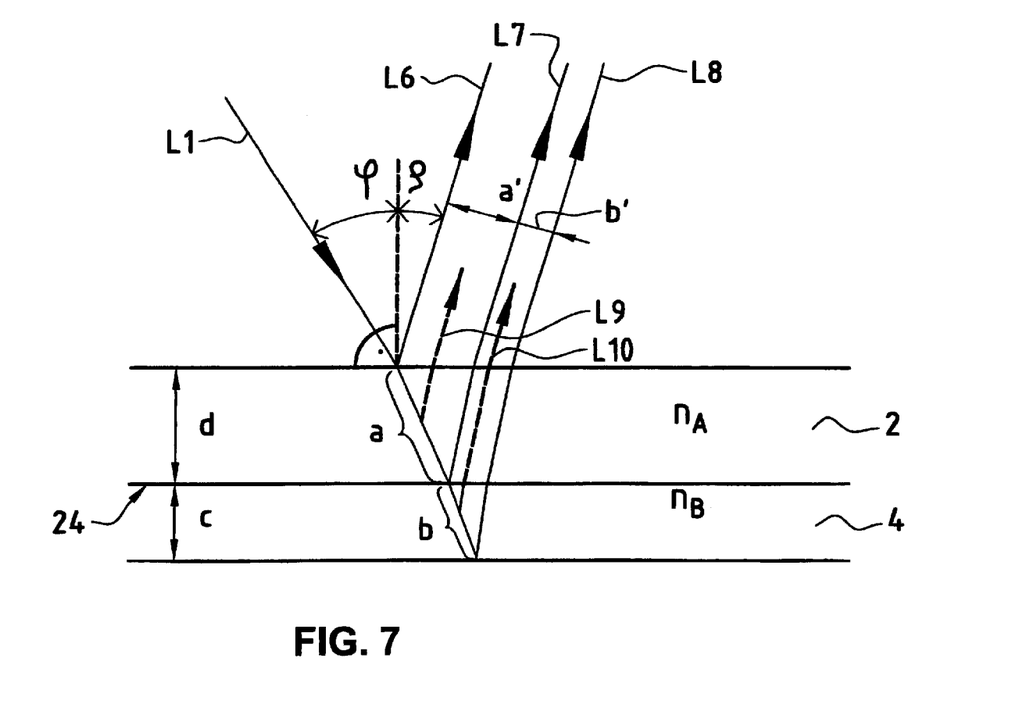
FIG. 7 shows a model of layers illustrating schematically the use of the contact element as calibrating element in determining the corneal thickness based on light scattering, fluorescence or diffuse reflection.

Illustrated schematically in FIG. 7 is the use of the contact element 2 as calibrating element in determining the thickness c of the cornea 4 based on light scattering, fluorescence or diffuse reflection. Light scattering and fluorescence can occur in the cornea 4 and in the contact element 2. A semi-transparent contact element 2 is preferably used to achieve a sufficient scattering of the incident light ray L1, which stands for all the (first) light waves projected by the light source 1', by way of example. Substances providing fluorescence or contrast-enhancing agents can also be added to the tear film, however. The tear film between the contact element 2 and the cornea 4 is not shown in FIG. 7. Diffuse reflection can be generated at the boundary surfaces of the contact element 2. The distances a' and b', shown in FIG. 7, between the reflected light rays L6 (third light waves), L7 and L8 (second light waves) are measured, for instance via a CCD camera. The light rays (light waves) L9 and L10 shown in broken lines in FIG. 7 should indicate that, with methods based on light scattering or fluorescence, light waves are also scattered in the interior of the contact element 2, respectively in the interior of the cornea 4. It is to be noted that the rays L6, L7, L8 represent only the main rays of the optical system of the registering means E, the totality of the reflected, respectively scattered, light rays L6, L7, L8 being projected into a further spatial area. Depending upon the optical system, the main rays L6, L7, L8 are parallel, as shown in FIG. 7 (telecentric image), or convergent. With convergent rays, a' and b' are no longer constant, and the image, dependent upon the imaging scale, of the distances a and b is measured. Also with this type of method, a simplified evaluation results if a contact element 2 is selected with a refraction index $n_A$ corresponding to the refraction index $n_B$ of the cornea 4. Then the thickness c of the cornea 4 results from the measured path lengths a' and b' as well as from the thickness d of the contact element 2:

$$c = b'\frac{d}{a'}$$

As with methods with specular reflection, the advantage results that only the ratio of the distances a' and b', or respectively of the images of a and b, has to be measured. With systems with non-telecentric imaging, the relevant imaging scale must be known during the sole measurement of a and b, but not if only the ratio is determined. If a and b do not lie tightly close together in the imagery, even distorted images do not matter since linear interrelationships can be taken in small image areas and thus the ratio of a and b can be precisely determined.

If $n_A$ and $n_B$ are not the same, the incidence angle $\Psi$ and the exit angle $\rho$ (refraction angle) must be known in addition to the refraction indexes $n_A$ and $n_B$ and the thickness d of the contact element 2. A precise measurement of the angles $\Phi$ and $\rho$ can be carried out, for instance via the contact element 2, since its surface can be very precisely manufactured compared to the surface character of the cornea 4. If the angles $\Phi$ and $\rho$ are kept constant, for example through an equidistant (parallel) displacement of the measuring head 8 used for the optical measuring method (see FIG. 4), respectively of the light source 1', to the contact surface of the (plane-parallel) contact element 2, then the thickness c of the cornea 4 can be also determined from the additional path length b' alone after one-time calibration (respectively determination of Φ and ρ). More favorable conditions result for the measurement of the distance b' if $n_B > n_A$ is selected ( the value of b' will be bigger). With non-telecentric imaging, once again the imaging scale must be known. Again the above-mentioned advantages result if the position of the contact element 2 can be determined and the contact surface area 24 is known sufficiently precisely. Thus the contact surface area 24 can be used as a reference here too, with respect to which the cornea 4 can be measured. It is to be mentioned here moreover that the angles Φ and ρ can be determined with reference to trigonometric ratios. If, for example, one considers the triangle described by the light rays L1, L6 and L7 in the contact element 2 in FIG. 7, one of the angles Φ and ρ can be calculated as a function of the other via trigonometric ratios, with given path length a', thickness d and refraction index $n_A$; that means that only one of the angles Φ and ρ has to be known. Here, too, advantages result from the use of contact elements 2 of known thickness d.

The following optical methods, which are based on diffuse reflection or respectively light scattering, can be used, for example: a single light ray (in combination with a one-dimensional scanner as light section, in combination with a two-dimensional scanner for surface registration), a plurality of light rays, light section methods (e.g. based on slit lamps or one-dimensionally scanned single light ray; in combination with a one-dimensional scanner for surface registration), stripe projection methods (a plurality of light sections) or photogrammetrical methods with structured illumination.

The following optical methods, which are based on fluorescence, can be used, for example: multi-photon excitation via focused light or multi-photon excitation only in focus with use of short pulses (femto pulses).

Figure 8A:
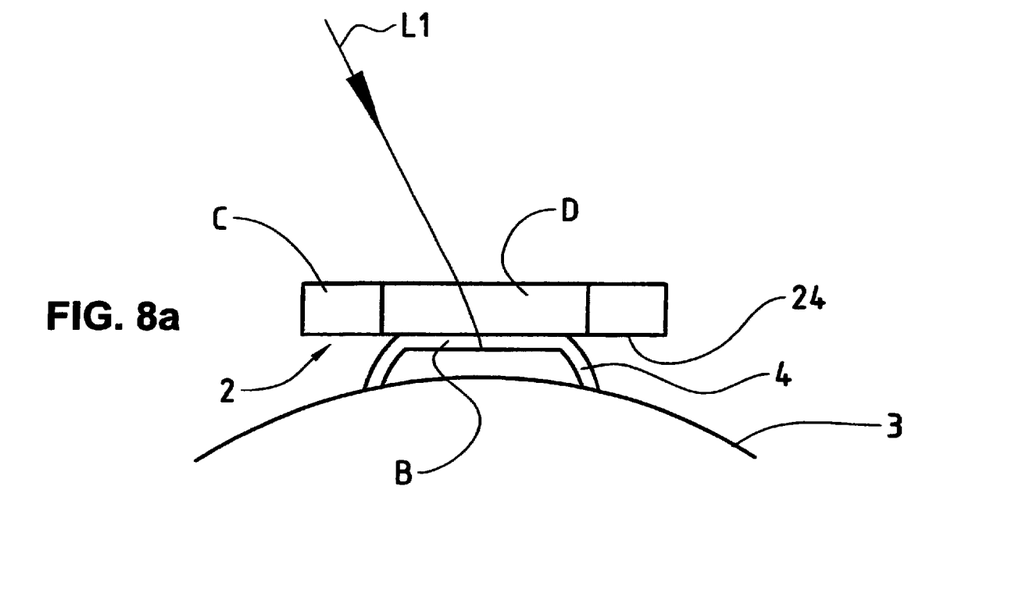
FIG. 8a shows a side view illustrating schematically an embodiment variant in which the contact element has a semi-transparent region, situated outside the area of measurement of the cornea on which the contact element is placed on the cornea.
Figure 8B:
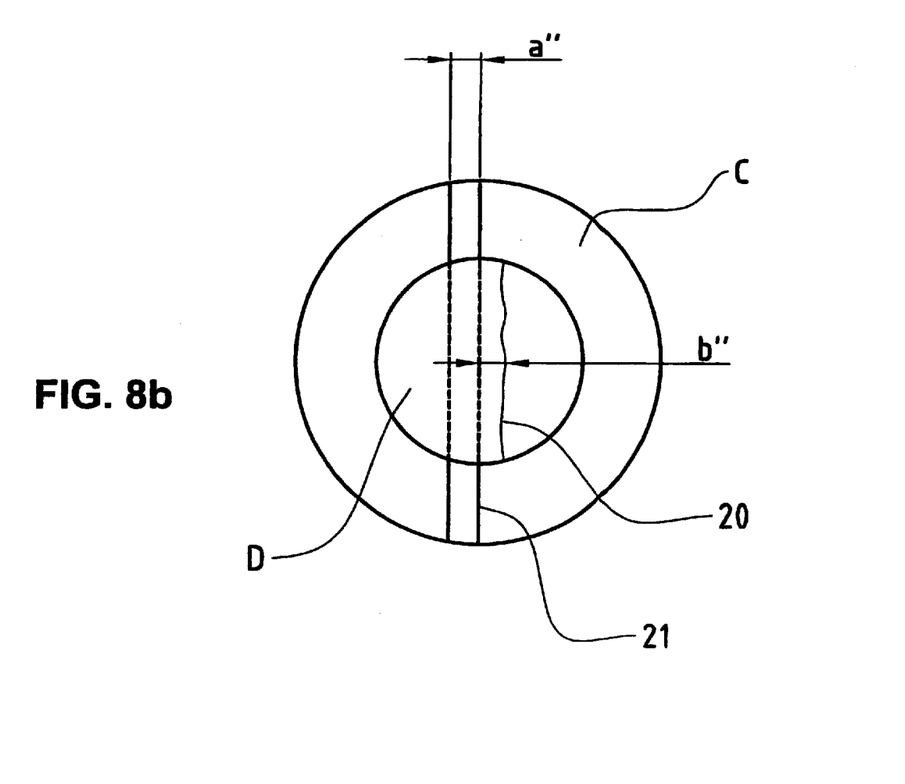
FIG. 8b shows a view from above illustrating schematically an embodiment variant in which the contact element has a semi-transparent region, situated outside the contact area of the cornea on which the contact element is placed on the cornea.

Illustrated schematically in FIGS. 8a and 8b is one embodiment variant for methods based on light scattering or fluorescence or diffuse reflection in which the contact element 2 has a semi-transparent region C which surrounds a transparent region D of the contact element 2 over the contact area B (for example the flattened area B in FIG. 8a) of the cornea 4. Measured are the distances a" and b" shown in FIG. 8b, the distance b" changing locally depending upon the corneal thickness. This embodiment variant has the advantage that even with use of a wide light beam the line 21 in the region C as well as the line 20 in the region D have a very good contrast to the background, and thus can be well detected. An advantage of this variant is that the semi-transparent region C of the contact element 2 does not cover the area B to be measured of the cornea 4.

Figure 4:
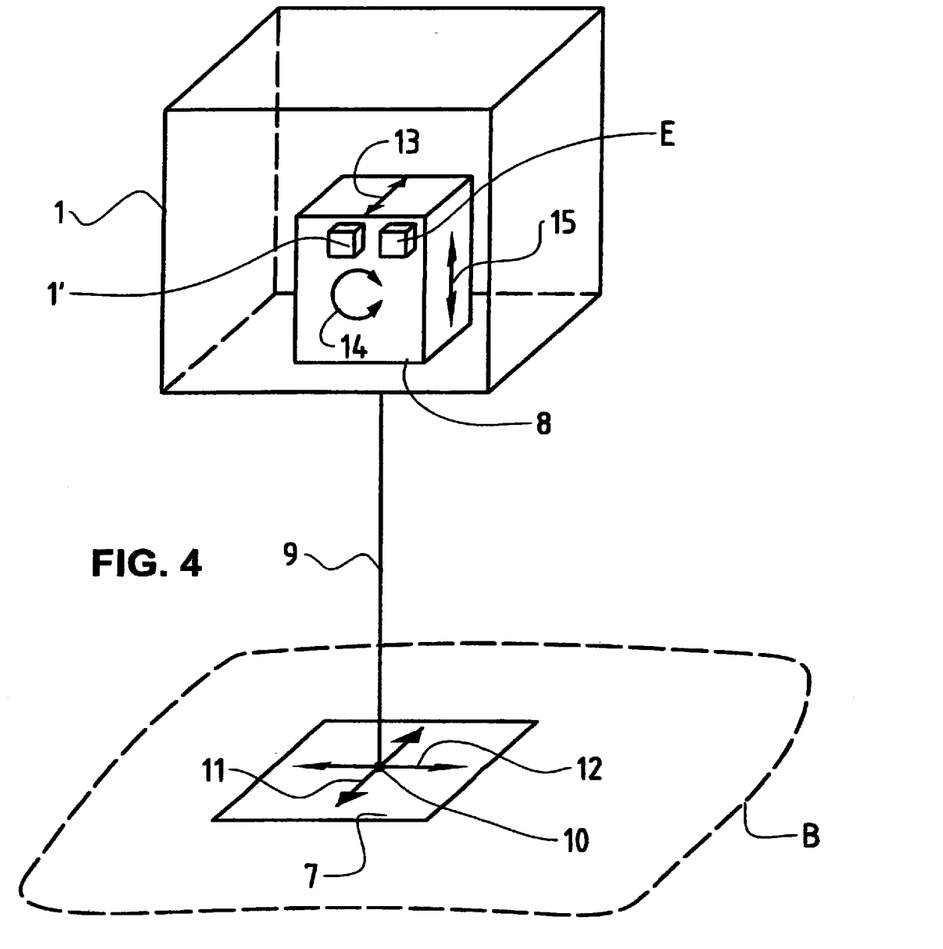
FIG. 4 shows a block diagram illustrating schematically an optical measuring apparatus which comprises an optical measuring head with a light source and with registering means, and which registers a measurement area in points.

As shown in FIG. 4, the optical measuring apparatus 1 comprises an optical measuring head 8 with the light source 1'. The optical measuring head 8, respectively the light source 1', is configured in such a way that the light waves L1 can be projected at least in points in a two-dimensional measuring the contact area B into and onto the cornea 4, so that the thickness of the cornea 4 can be determined at one or more places of the measuring area 7. In an embodiment with a plurality of contact areas B, the measuring area could also comprise regions between the contact areas. The optical measuring head 8 for registration of the measuring area 7 is moved mechanically, according to the embodiment variant, for example according to whether a method is used operating point-wise, line-wise (stripe-wise) or area-wise. The optical measuring head 8 further comprises the registering means E, dependent upon the optical method employed, for registration of the light waves L3 and L4 (see FIG. 6), respectively L7, L8 and L10 (see FIG. 7), which are reflected by the cornea 4, and the light waves L2 (see FIG. 6), respectively L6 and L9 (see FIG. 7), which are reflected by the contact element 2. In an embodiment variant, light source 1' and registering means E move with the optical measuring head 8. In a further embodiment variant, only the light source 1' moves, and the registering means E remain stationary. Shown in FIG. 4 is a method operating point-wise with a light ray 9 projected by the light source, with the measuring point 10, and with the directions of movement 11 and 12 in the measuring area 7 of the cornea 4. As indicated by way of example in FIG. 4, the optical measuring head 8 carries out a translation 13 for the direction 11, and the optical measuring head 8, respectively the light source 1', carries out a rotation 14 for the direction 12. The movements for the directions 11 and 12 can also be carried out through two translations or through two rotations. For certain applications, for example in the case of oblique positioning of the contact element 2, a vertical direction of movement 15 can also be additionally required in order to keep the measuring point in the vertical measuring area.

Figure 5:
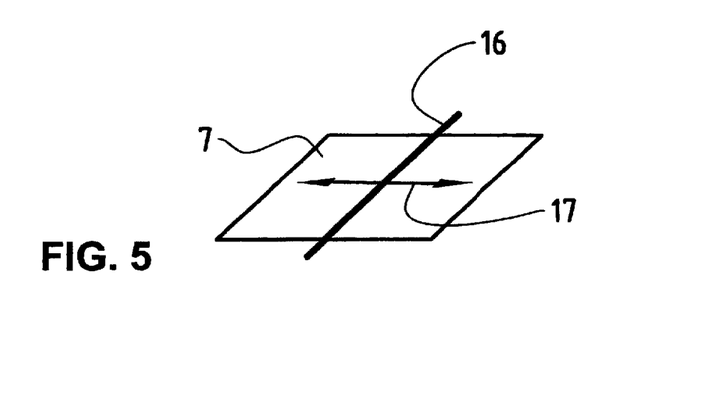
FIG. 5 shows a block diagram illustrating schematically a two-dimensional measuring area in which measuring is carried out along a line.

Shown in FIG. 5 is a method operating line-wise (stripe-wise), for example with a light section 16 projected by the light source 1' in which only the direction of movement 17 remains for registering the measuring area 7 when the length of the light section 16 covers the width of the measuring area 7. The remaining direction of movement 17 can be carried out through corresponding movement of the optical measuring head 8, respectively of the light source 1'. In a method operating with area-wise (not shown) in which areas that are larger than the measuring area 7 are illuminated, directions of movement can be eliminated entirely.

Figure 2:
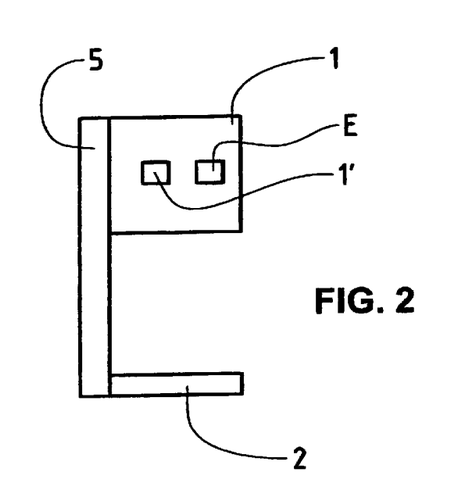
FIG. 2 shows a block diagram illustrating schematically an embodiment variant of the device configuration in which the optical measuring apparatus is firmly connected to the contact element by means of a member.

As shown in FIG. 2, in an embodiment variant, the optical measuring apparatus 1 is firmly connected to the contact element 2 by means of a member 5. For the method presented above, which requires knowledge of the position of the contact element 2, the connection of the contact element 2 to the optical measuring apparatus 1 needs to be fixed only during the determination of position and the subsequent measurement. That means a position calibration or long-term stability is not necessary, so that detachable contact elements 2 can be used which have different, predefined thicknesses d, for example, and/or are disposable.

It should be pointed out here that it is also possible to integrate the light source 1' into the contact element 2, for example in the embodiment of one or more light-emitting diodes. In the same way, registering means E can be integrated into the contact element 2. The latest developments in the field of MEMS (micro electromechanical systems) show the feasibility of such micro integrations.

Figure 3:
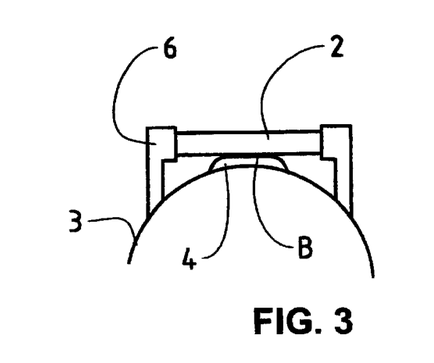
FIG. 3 shows a block diagram illustrating schematically a contact element fixed on the eye, or respectively on the cornea, through a device.

In the embodiment variant shown schematically in FIG. 3, the contact element 2 is fixed on the eye 3, respectively on the cornea 4, through partial suction, for example by means of a suction ring 6 known to one skilled in the art. If the contact element 2 is both fixed on the cornea 4 as well as connected to the optical measuring apparatus 1, a costly tracking of the eye 3 during the measurement is completely eliminated. The patient does not have to be positioned in a time-consuming and complex way in front of the measuring apparatus; he can even be examined in a lying position, and moreover does not need to focus his eye 3 on a target object.

The optical measuring apparatus 1 also comprises processing means which depend upon the optical method applied as well as upon the registering means E used therefor. The processing means comprise, for example, a processor with connected data save store and program memory in which executable software programs are stored. The software programs are programmed for control of the optical measuring head 8, respectively of the light source 1', as well as for control of the registering means E and for evaluation of the registered reflected light waves L2, L6 and L9 (third light waves) as well as L3, L4, L7, L8 and L10 (second light waves) for determining the corneal thickness over a two-dimensional measuring area 7 (see FIG. 4). The measured corneal thicknesses can be shown, for example, numerically and/or graphically on a screen, or printed out. In an embodiment variant, the measurement data can also be shown in relation to the respective eye 3, structures such as the iris, the retina or the limbus being suitable as reference marks of the eye 3. If an optical method for determination of the corneal thickness is used that is not suitable for generating or registering such reference marks on the eye 3 and on the contact element 2, this can be achieved, for instance, by means of an additional camera and a suitably disposed semi-permeable mirror.

Figure 9A:
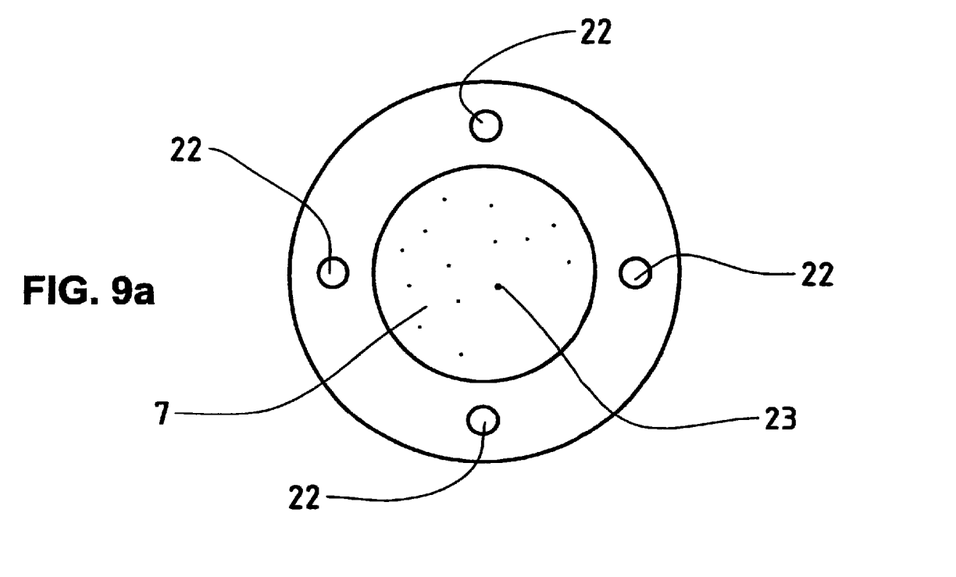
FIG. 9a shows a view from above illustrating schematically a contact element with reference marks.
Figure 9B:
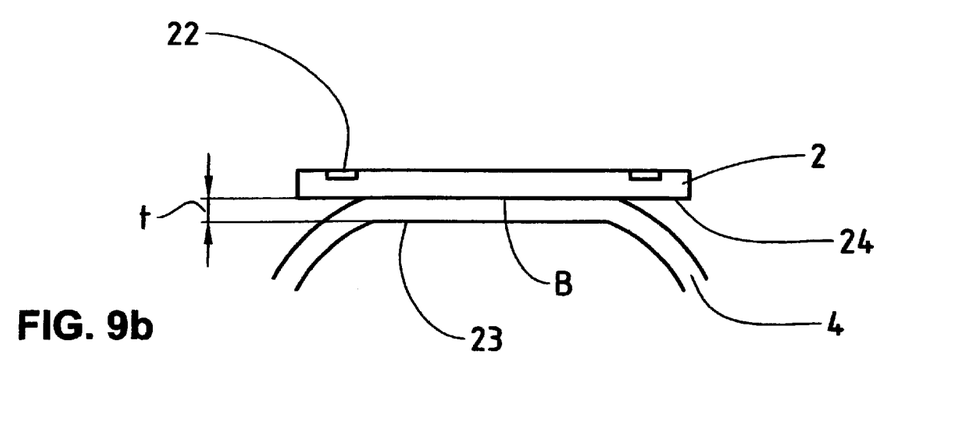
FIG. 9b shows a side view illustrating schematically a contact element with reference marks which is placed on a cornea.

Reference marks used for determining the position of the contact element 2 can be applied to the contact element 2 in the region over the contact area B (for example the flattened area B in FIG. 9*b*) of the cornea 4 or outside this region. Reference marks can be active (i.e. self-illuminating or projected) or passive (i.e. indirectly illuminated). Specular reflection, diffuse reflection, light scattering or fluorescence can be used to generate reference marks. Shown, by way of example, in FIG. 9*a* is a contact element 2 on which the reference marks 22 have been applied outside the measuring area 7, the measuring area 7 being a sub-area of the contact area B of the cornea 4 or coinciding with the contact area B. The reference marks 22 on the contact element 2 can be used to determine the position of the contact element 2 and to carry out measurements, in accordance with the determined position, relative to the contact surface area 24 shown in FIG. 9*b,* in this example a planar, flattened surface. From this the advantage results that measurements in succession, for example measurements of individual measuring points 23, with respect to a physically existing reference basis, in particular the contact surface area 24, can be registered so that, for example, only depth measurements t of measuring points 23 on the inner corneal surface have to be carried out in order to determine the corneal thickness. Since reference surfaces can be produced and determined with very high precision, the determination of the corneal thickness for a measuring point 23 is reduced to a measuring value t, so that a higher precision can be achieved than with the subtraction of two measurement values for a measuring point. Furthermore, the measuring area of the optical method applied can be limited if only the inner corneal surface (contact surface area 24) is measured, for instance an autofocus sensor or light section sensor would have to focus only on the inner corneal surface, which further increases the measuring speed.

Figure 10:
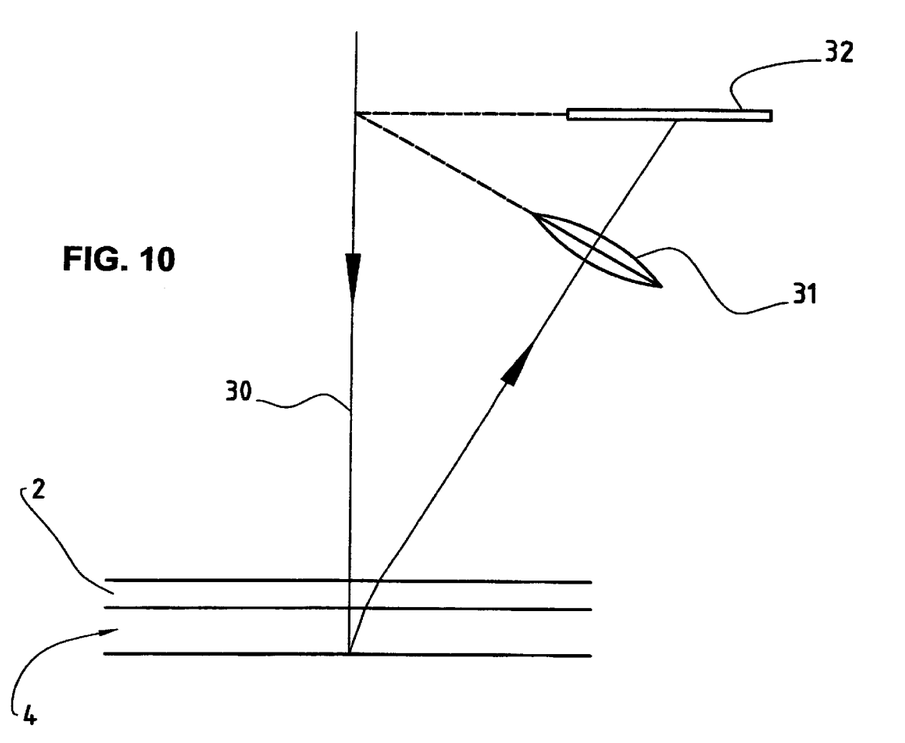
FIG. 10 shows as diagram illustrating schematically a device configuration according to the Scheimpflug condition.

Shown in FIG. 10 is a configuration for methods based on light scattering or fluorescence or diffuse reflection in which the image converter 32 and the lens 31 of the registering means E are disposed according to the Scheimpflug condition. The refraction of the light rays caused by the contact element 2 and the cornea 4 must thereby be taken into consideration in the arrangement of the registering means E. In general, the Scheimpflug condition can thereby be well approximated. Depicted in FIG. 10, by way of example, on the image converter 32 in Scheimpflug configuration is a light section 30, generated perpendicular to the contact element 2, via the lens 31. With plane-parallel contact element 2, this advantageous configuration can be shifted parallel to the surface, respectively to the contact surface area of the contact element 2, no continual adaptation of the projection of the light section being necessary owing to the lacking corneal curvature. Because of the lacking corneal curvature, moreover, the depth of focus area of the light source 1' and of the registering means E can be reduced and thus the resolution heightened. A further advantage of this arrangement is that, through the direction of the incident light rays, measuring is carried out strictly perpendicular to the corneal surface.

Finally, it should be mentioned here that, depending upon the embodiment variant and the selected optical method, the associated light source 1' and the associated registering means E and processing means can be implemented in a device configuration consisting of a plurality of individual components, or that is achieved as a compact device, which is suitable in particular for mobile employment when it is designed as a portable hand-held device. Through the proposed use of the contact element 2 as a reference for measurement of the corneal thickness, the measuring time, effort and complexity, and thus the expense in technical devices, can be reduced compared to the state of the art since, on the one hand, the cornea 4 is aligned through the contact surface 24, G2 of the contact element 2, i.e. brought into a defined position, and, on the other hand, the thickness d of the contact element 2 can be used for measuring.

What is claimed is:

1. A method for determining a corneal thickness of an eye, in particular a human eye, by means of light waves, first light waves being projected onto and into a cornea, and second light waves, reflected by the cornea;

being registered for determining the corneal thickness; wherein
a contact element is placed on at least one contact area of the cornea; and
the first light waves are projected through the contact element onto and into the cornea.

2. The method according to claim 1, wherein the first light waves are projected at least in points into a two-dimensional measuring area of the at least one contact area onto and into the cornea, and the corneal thickness is determined at one or more places of the measuring area.

3. The method according to claim 2, wherein a contact element is used having a predefined thickness, and the thickness of the contact element is co-used for determining the corneal thickness.

4. The method according to claim 3, wherein the cornea is brought into a defined state by means of a contact surface of the contact element.

5. The method according to claim 3, wherein a plane-parallel contact element is used.

6. The method according to claim 5, wherein, additionally, third light waves, which are reflected by the contact element, are registered for determining the corneal thickness.

7. The method according to claim 1, wherein the contact element is fixed on the cornea or on the eye.

8. The method according to claim 1, wherein an at least partially semi-transparent contact element is used which makes possible a scattering of the first light waves through light diffusion or fluorescence in the contact element or through diffuse reflection at its boundary surfaces.

9. The method according to claim 1, wherein a contact element is used, a refraction index of which corresponds to a refraction index of the cornea.

10. The method according to claim 1, wherein a light source, from which the first light waves are projected, and/or registering means, which register the reflected light waves, are disposed according to the Scheimpflug condition in order to avoid defocusing.

11. The method according to claim 1, wherein the first light waves are projected with a constant incidence angle on the cornea.

12. The method according to claim 11, wherein a light source, from which the first light waves are projected, is moved at a constant distance from the contact surface of the contact element.

13. The method according to claim 1, wherein reflected light waves are registered at constant viewing angle.

14. The method according to claim 1, wherein registering means, which register the reflected light waves, are moved at a constant distance from the contact surface of the contact element.

15. The method according to claim 1, wherein a light source, from which the first light waves are projected, and registering means, which register the reflected light waves are connected to the contact element.

16. A device configuration for determining a corneal thickness of an eye, in particular a human eye, by means of light waves, comprising at least a light source for projection of first light waves onto and into a cornea, registering means for registering second light waves, which are reflected by the cornea, and processing means for determining the corneal thickness from the registered second light waves; wherein the device configuration comprises a contact element which is placeable on at least one contact region of the cornea; and the light source is disposed in such a way and the contact element is designed such that the first light waves are projected through the contact element onto and into the cornea.

17. The device configuration according to claim 16, further comprising:

means of projecting the first light waves at least in points in a two-dimensional measuring area of the at least one contact region onto and into the cornea, wherein the registering means and the processing means are configured in such a way that the corneal thickness is determined at one or more places of the measuring area.

18. The device configuration according to claim 17, wherein the contact element has a predefined thickness, and the registering means and the processing means are configured in such a way that the thickness of the contact element is co-used for determining the corneal thickness.

19. The device configuration according to claim 18, wherein the contact element has a contact surface by means of which the cornea is brought into a defined state.

20. The device configuration according to claim 18, wherein the contact element is plane-parallel.

21. The device configuration according to claim 20, wherein the registering means are configured in such a way that, additionally, third light waves, which are reflected by the contact element, are registered, and the processing means is configured in such a way that the corneal thickness is determined taking into account the registered third light waves.

22. The device configuration according to claim 16, wherein it comprises means of fixing the contact element on the cornea or on the eye.

23. The device configuration according to claim 16, wherein the contact element is at least partially semi-transparent and makes possible a scattering of the first light waves through light diffusion or fluorescence in the contact element or through diffuse reflection at its boundary surfaces.

24. The device configuration according to claim 16, wherein the contact element has a refraction index which corresponds to a refraction index of the cornea.

25. The device configuration according to claim 16, wherein the light source and/or the registering means are disposed according to the Scheimpflug condition in order to avoid defocusing.

26. The device configuration according to claim 16, wherein it comprises means of projecting the first light source with constant incidence angle on the cornea.

27. The device configuration according to claim 16, wherein the registering means are configured in such a way that reflected light waves are registered at a constant viewing angle.

28. The device configuration according to claim 26, wherein it comprises means of moving the light source at a constant distance from the contact surface of the contact element.

29. The device configuration according to claim 16, wherein it comprises means of moving the registering means at a constant distance from the contact surface of the contact element.

30. The device configuration according to claim 16, wherein it comprises means of connecting the light source and the registering means to the contact element.

* * * * *